United States Patent [19]

Kato et al.

[11] Patent Number: 4,960,910
[45] Date of Patent: Oct. 2, 1990

[54] OXETANE DERIVATIVES

[75] Inventors: Kuniki Kato, Yono; Tomohisa Takita, Asaka; Shigeru Nishiyama; Shosuke Yamamura, both of Yokohama, all of Japan

[73] Assignee: Nippon Kayaku Kabushiki Kaisha, Tokyo, Japan

[21] Appl. No.: 365,743

[22] Filed: Jun. 13, 1989

[51] Int. Cl.$^5$ .......................................... C07D 305/08
[52] U.S. Cl. ................................................. 549/510
[58] Field of Search ........................................ 549/510

[56] References Cited

PUBLICATIONS

N. Shimada, et al., *J. Antibiotics*, "Oxetanocin, a novel nucleoside from bacteria," 39(11), pp. 1623–1625 (1986).

*Primary Examiner*—Richard L. Raymond
*Assistant Examiner*—Mark W. Russell
*Attorney, Agent, or Firm*—Henry C. Nields

[57] ABSTRACT

The present invention relates to an oxetane derivative represented by the general formula (I):

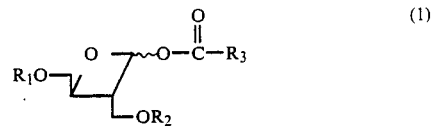

wherein $R_1$ and $R_2$ are each an acyl group and $R_3$ is a hydrogen atom or a lower alkyl group, which is useful as an intermediate for the preparation of a compound having a (bishydroxymethyl)oxetane structure in its saccharide moiety, for example, oxetanosine, and a process for the preparation of the same.

3 Claims, No Drawings

OXETANE DERIVATIVES

FIELD OF THE INVENTION

The present invention relates to a novel oxetane derivative useful as an intermediate for the preparation of an oxetane nucleoside derivative which is expected as a drug and a process for the preparation of the same.

BACKGROUND OF THE INVENTION

Up to this time, only linear and five- or six-membered ring saccharides have been known as a saccharide moiety of a nucleoside consitting a nucleic acid. Recently, however, oxetanocin having a four-membered ring skeleton (oxetane ring) which is represented by the following formula:

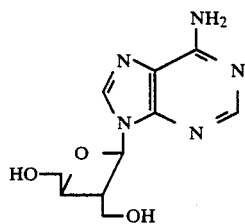

has been isolated from a natural substance for the first time as an aberrant constituent of a nucleic acid (see N. Shimada et al., J. Antibiotics, 39, 1623 (1986)).

The oxetanocin has antibacterial, antiviral and antitumor activities, so that it has been expected as a drug.

In order to facilitate the preparation of oxetanocin or various drivatives having the same saccharide moiety as that of oxetanosine, the development of a four-membered ring saccharide which serves as an intermediate for the preparation has been expected.

SUMMARY OF THE INVENTION

The inventors of the present invention have extensively studies and have succeeded in the synthesis of an oxetane compound which has not been known at all and is represented by the general formula (I):

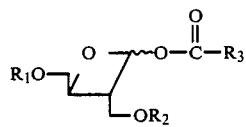

wherein $R_1$ and $R_2$ are each an acyl group and $R_3$ is a hydrogen atom or a lower alkyl group. Further, they have found that an oxetane nucleoside represented by the general formula (II):

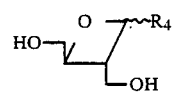

wherein $R_4$ is a nucleic acid base, can be prepared by the condensation of an oxetane compound represented by the general formula (I) with a nucleic acid base.

The present invention has been accomplished on the basis of this finding.

DETAILED DESCRIPTION OF THE INVENTION

The compound of the present invention can be prepared according to the process which will be described hereinbelow.

(i) Preparation of a compound represented by the general formula (I)

A compound represented by the general formula (I) can be prepared from a compound represented by the general formula (III):

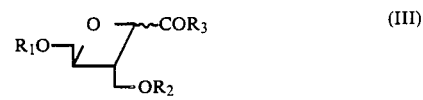

wherein $R_1$, $R_2$ and $R_3$ are as defined above, according to the Baeyer-Villiger reaction. The Baeyer-Villiger reaction may be carried out by reacting a compound of the general formula (III) with a peracid, for example, an organic peracid such as performic, peracetic perbenzoic, m-chloroperbenzoic or monoperphthalic acid or a peroxo acid such as peroxodisulfuric, peroxosulfuric or peroxophosphoric acid in a solvent such as chloroform, methylene chloride, ethyl acetate, benzene, toluene or a mixture thereof at a temperature of 0° C. to the reflux temperature of the solvent, preferably about 1° to about 30° C., for about 1 to about 30 hours. The amount of the peracid to be used is about 1 to about 5 equivalents, preferably about 1 to about 2 equivalents per equivalent of the compound of the general formula (I) used.

In the above general formulas (I) and (III), $R_1$ and $R_2$ are each a $C_{1\sim4}$ lower acyl group such as an acetyl, propionyl or butyroyl group, a carbo($C_{1\sim4}$)-alkoxycarbonyl group of oxalate type, a ($C_{1\sim4}$)-alkoxycarbonyl-methylcarbonyl group of malonate type or an aromatic acyl group such as a benzoyl or substituted benzoyl group, while $R_3$ is a hydrogen atom or a lower alkyl group such as a methyl, ethyl or propyl group.

(ii) Preparation of a compound represented by the general formula (II)

A compound represented by the general formula (II) can be prepared by the deacylation of a compound of the general formula (IV) prepared according to the following reaction scheme (A): (A)

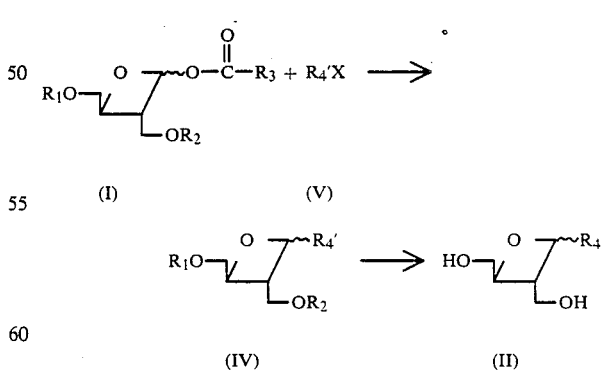

wherein $R_1$, $R_2$ and $R_3$ are each as defined above; $R_4'$ is a nucleic acid base, the functional groups of which are protected; $R_4$ is a nucleic acid base; and X is a reactive group such as a silyl group.

The reaction represented by the reaction scheme (A) may be carried out by reacting a compound represented by the general formula (I) with a nucleic acid base represented by the general formula (V) and a silylated derivative thereof at an equivalent ratio between about 1:1 and 1:10, preferably between about 1:2 and 1:5 in the presence of boron trifluoride etherate, tin tetrachloride, titanium tetrachloride, zinc chloride or magnesium bromide in an organic solvent such as dichloromethane, chloroform, 1,2-dichloroethane, acetonitrile, benzene, toluene or chlorobenzene at a temperature of 0° C. to the reflux temperature and purifying the reaction product by column chromatography or the like.

The use of a compound of the general formula (I) wherein $R_2$ is an alkoxycarbonylacyl group such as an oxalate is preferred in order to obtain a compound having the same configuration as that of oxetanocin.

A compound of the general formula (II) can be prepared by the deacylation of a compound of the general formula (IV) as prepared above with acid or alkali according to a conventional process.

(iii) Preparation of a compound represented by the general formula (III)

A compound represented by the general formula (III):

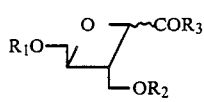   (III)

wherein $R_1$, $R_2$ and $R_3$ are each as defined above, can be prepared from a known compound (VI) (see Marcus A. Tius and Abdul H. Fauq, J. Org. Chem., 48, 4131 (1983)) according to the following reaction scheme:

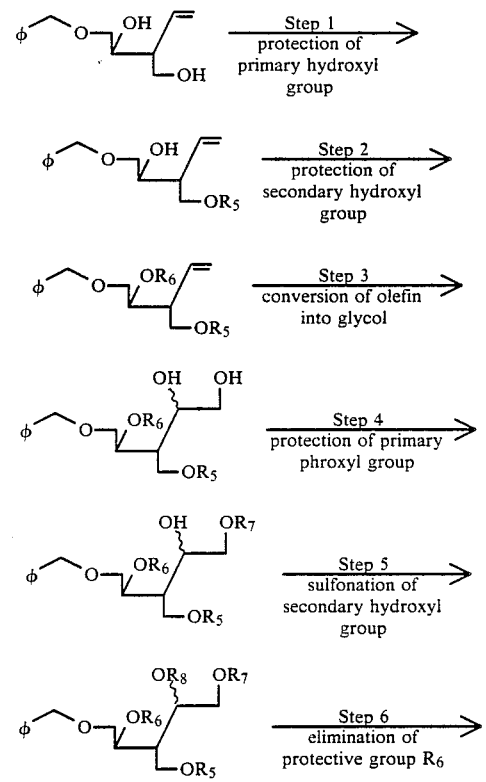

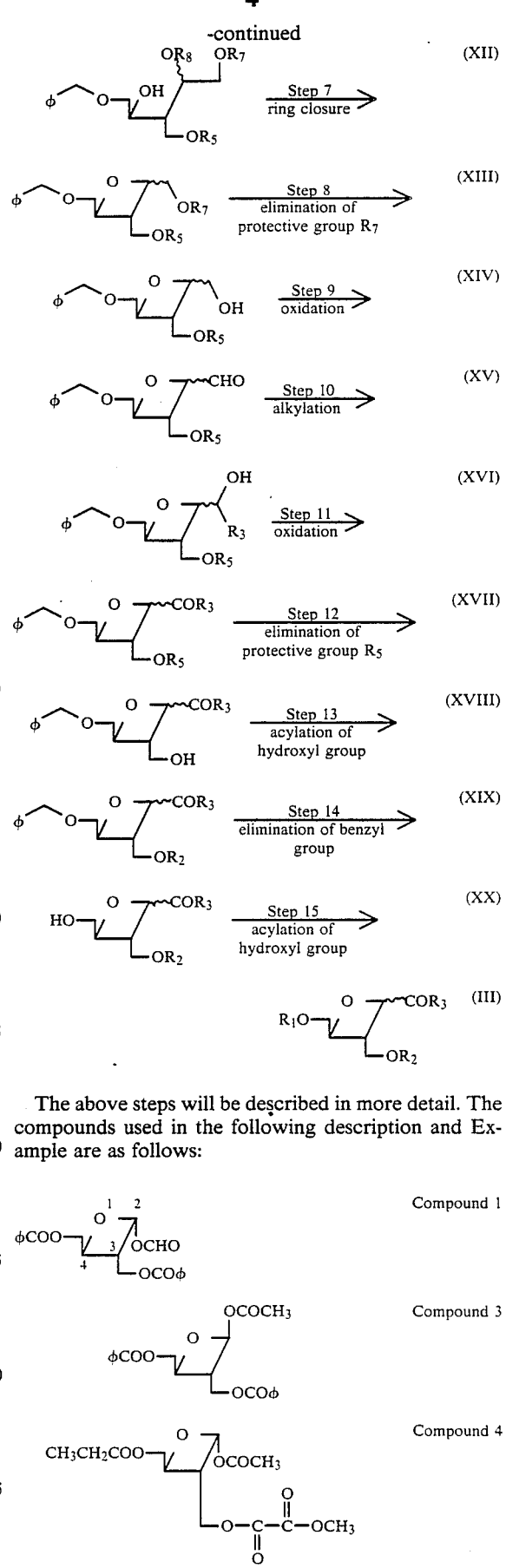

The above steps will be described in more detail. The compounds used in the following description and Example are as follows:

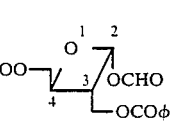

Compound 1

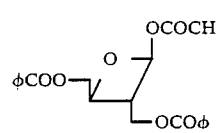

Compound 3

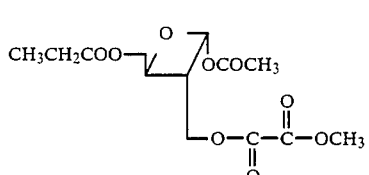

Compound 4

5
-continued

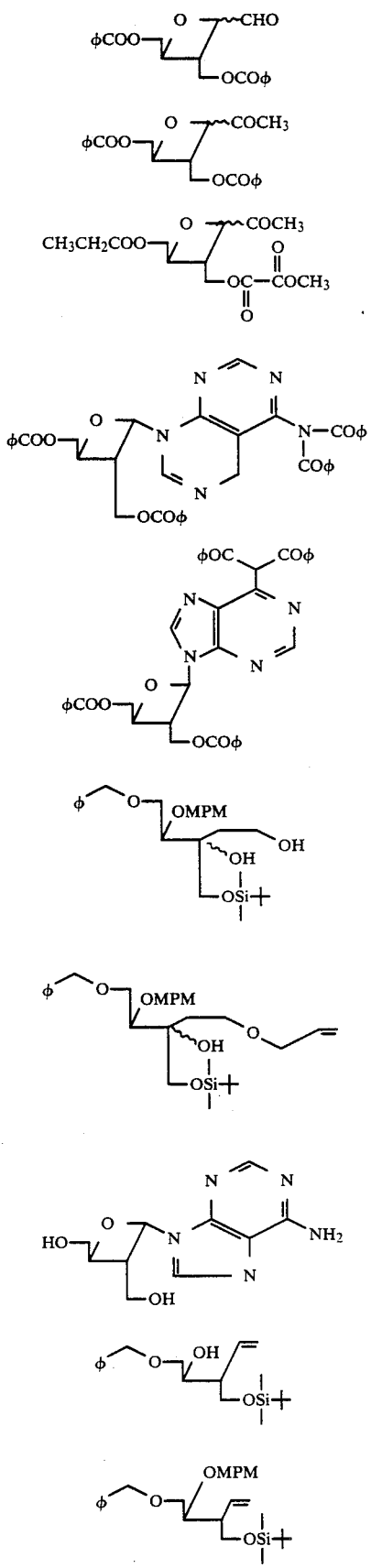

Compound 5

Compound 6

Compound 7

Compound 8

Compound 9

Compound 13

Compound 14

Compound 10

Compound 11

Compound 12

6
-continued

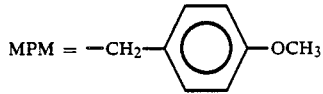

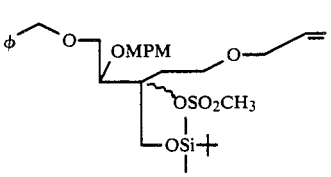
Compound 15

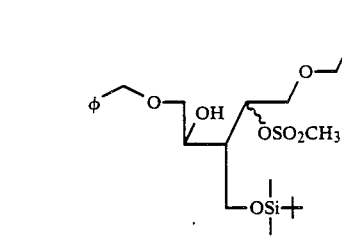
Compound 16

Step 1

It is preferred that the protective group $R_5$ for the primary hydroxyl group be one which can withstand the elimination of Steps 6 and 8. Suitable examples thereof include benzyl, p-methoxybenzyl, t-butyldimethylsilyl and t-butyldiphenylsilyl groups.

The reaction of Step 1 may be carried out by reacting a compound of the general formula (VI) with benzyl chloride or p-methoxybenzyl chloride in the presence of a basic catalyst such as sodium hydride, potassium hydride, butyllithium or alkoxide of sodium or potassium in an inert solvent such as tetrahydrofuran, dimethylformamide, ether, benzene or toluene at a temperature of 0° C. to the reflux temperature. Further, the silylation may be carried out by reacting it with a silylating agent in the presence of a basic catalyst such as triethylamine or imidazole in methylene chloride or dimethylformamide at a temperature of 0° C. to room temperature.

Preparation of Compound (11)

Compound (VI)/t-butyldimethylsilyl chloride/imidazole/DMF, room temperature and 5 hours, yield:82%

Step 2

It is preferred that the protective group $R_6$ for the secondary hedroxyl group be one which does not exert any effect on the groups $R_5$, $R_7$ and $R_8$ and the benzyl group of the compound (XI) in the elimination of Step 6. Suitable examples thereof include p-methoxybenzyl, t-butyldimethylsilyl and t-butyldiphenylsilyl groups. The reaction conditions may be the same as those of Step 1.

Preparation of Compound (12)

Compound (11)/sodium hydride/p-methoxybenzyl chloride/dimethylformamide, room temperature and one night, yield: 76%

Step 3

The conversion of the olefin into a glycol may be carried out by oxidation using osmium tetraoxide or by epoxidizing the olefin and hydrolyzing the epoxide. The oxidation method may be carried out by using an equimolar amount of osmium tetraoxide or by using a catalytic amount of osmium tetraoxide with an oxidizing agent such as N-methylmorpholine oxide, t-butyl hydroperoxide or hydrogen peroxide.

Preparation of Compound (13)

Compound (12)/0.01 equivalent of osmium tetraoxide/N-methylmorpholine oxide/water-acetone-t-butyl alcohol, room temperature and one day, yield: 92%

Step 4

It is preferred that the protective group $R_7$ for the primary hydroxyl group be one which is not affected by the elimination of the protective group $R_6$ in Step 6 and does not exert any effect on the other protective groups and the formed oxetane ring in the elimination of Step 8. A suitable example thereof is an allyl ether group.

Preparation of Compound (14)

Compound (13)/sodium hydride/allyl bromide/tetrahydrofuran, room temperature and one night, yield: 82%

The compound (X) thus prepared in this step is a mixture of an R-isomer and an S-isomer. These isomers can be easily separated from each other by, for example, silica gel chromatography using a hexane/ethyl acetate mixture as the solvent. The R-isomer gives a $2\alpha$ isomer of a compound of the general formula (III), while the S-isomer gives a $2\beta$ isomer thereof.

Step 5

The sulfonating agent may be a conventional one such as methanesulfonyl chloride, benzenesulfonyl chloride or p-toluenesulfonyl chloride. The esterification may be carried out in the presence of a basic catalyst such as triethylamine, pyridine or N,N-dimethylaminopyridine.

Preparation of Compound (15)

Compound (14)/methanesulfonyl chloride/triethylamine/methylene chloride, room temperature and 3 hours, yield: 93%

Step 6

The conditions for the elimination of the protective group $R_6$ may be those while do not exert any effect on the other protective groups and the group $R_8$. When $R_6$ is a p-methoxybenzyl group, dichlorodicyanobenzoquinone (DDQ) is used, while when $R_6$ is a t-butyldimethylsilyl or t-butyldiphenylsilyl group, tetrabutylammonium fluoride or potassium fluoride is used.

Preparation of Compound (16)

Compound (15)/DDQ/methylene chloride-water, room temperature and 2 hours, yield: 86%

Step 7

The ring closure is preferably carried out by using a basic catalyst such as sodium hydride, potassium hydride or potassium t-butoxide. Namely, a sodium or potassium salt of the compound (XII) is reacted in an inert solvent such as ether, tetrahydrofuran, benzene or toluene at a temperature of 0° C. to the reflux temperature.

Preparation of Compound (17)

Compound (16)/sodium hydride/tetrahydrofuran, room temperature and one night, yield: 84%

Step 8

The elimination of the protective group $R_7$ may be carried out under such conditions as to exert no effect on the oxetane ring, the group $R_5$ and the benzyl group.

Preparation of Compound (18)

Compound (17)/RhCl($\phi_3$P)$_3$ (tris(triphenylphosphine) rhodium chloride)/DABCO (diazabicyclooctane)/ethanol-water, reflux for 6 hours, and then, mercury oxide/mercuric chloride/acetone, reflux for 2 hours, yield: 65%

Step 9

The oxidation may be carried out under such conditions as to exert no effect on the oxetane ring, the group $R_5$ and the benzyl group and is favorably carried out according to Swern oxidation or Pfitzner-Moffatt oxidation.

Preparation of Compound (19)

Compound (18)/dimethyl sulfoxide/oxalyl chloride/methylene chloride, $-45°$ C., 20 minutes, and then, addition of triethylamine, $-45°$ C., 30 minutes

Step 10

The alkylation of the compound (XV) may be carried out by reacting it with an organic alkyl metal compound such as a Grignard reagent or alkyllithium reagent in an inert solvent such as ether, tetrahydrofuran, benzene or toluene.

Preparation of Compound (20)

Compound (19)/methylmagnesium iodide/tetrahydrofuran-ether, 0° C., 2 hours, the overall yield of Steps 9 and 10: 87%

Step 11

The conditions for the oxidation may be the same as those of Step 9.

Preparation of Compound (21)

Compound (20)/dicyclohexylcarbodiimide/pyridine/trifluoroacetic acid/dimethyl sulfoxide/benzene, room temperature and one night, yield: 51%

Step 12

The elimination of the protective group $R_5$ may be carried out under such conditions as to exert no effect on the oxetane ring and the carbonyl group.

Preparation of Compound (22)

Compound (21)/tetrabutylammonium fluoride/tetrahydrofuran, room temperature and 2 hours, yield: 68%

Step 13

The acylation may be carried out by reacting the compound (XVIII) with an ordinary acyl halide in the presence of a base such as pyridine, triethylamine or N,N-dimethylpyridine as the catalyst in an inert solvent such as methylene chloride, benzene, toluene or ether.

Preparation of Compound (26)

Compound (22)/methyloxalyl chloride/pyridine, room temperature and 3 hours, yield: 30%

Step 14

The elimination of the benzyl group may be carried out under such conditions as to exert no effect on the oxetane ring, the carbonyl group and the acyl group $R_2$ and is favorably carried out by catalytic reduction with palladium/carbon or palladium hydroxide.

Preparation of Compound (27)

Compound (26)/palladium black/tetrahydrofuran, room temperature, 20 minutes

Step 15

The conditions for the acylation of the hydroxyl group may be the same as those of the acrylation of Step 13.

Preparation of Compound (7)

Compound (27)/propionyl chloride/pyridine, 0° C., one hour

The overall yield of Steps 14 and 15: 66%

The compounds represented by the general formulas I to XX can be each prepared as an optically pure one by an ordinary method such as a method of using an optically active column or a method of bonding an optically active resolution aid to the hydroxyl group contained therein and resolving the resulting compound. Alternatively, they can be each prepared as an optically pure one by replacing the protective group of the compound thus prepared by another protective group or by using an optically active precursor.

The compound represented by the general formula (I) according to the present invention is useful as an intermediate for the preparation of the compound represented by the general formula (II).

The present invention will now be described in more detail by referring to the following Examples.

EXAMPLE 1

Preparation of (2α, 3α, 4β)-2-formyloxy-3,4-dibenzoyloxymethyloxetane(-Compound 1)

0.05 ml of oxalyl chloride and 0.07 ml of dimethyl sulfoxide were added to a solution of 51.0 mg of (2α, 3α, 4β)-2-hydroxymethyl-3,4-dibenzoyloxymethyloxetane(Compound 28) in 2 ml of methylene chloride at −50° C. and the obtained mixture was stirred for 30 minutes, followed by the addition of 0.15 ml of triethylamine. The reaction was carried out for additional 20 minutes. The reaction mixture was diluted with chloroform, washed with water and a saturated aqueous solution of common salt, dried over anhydrous sodium sulfate and distilled under a reduced pressure to remove the solvent. The residue was purified with a preparative silica gel thin-layer plate to give 54.5 mg of an aldehyde compound (Compound 5). The aldehyde compound is unstable, so that it was used in the following step as such without any purification. The aldehyde compound was dissolved in 5 ml of methylene chloride, followed by the addition of 58.5 mg of m-chloroperbenzoic acid. The reaction was carried out at 4° C. overnight. The reaction mixture was concentrated in a vaccum at room temperature and purified by Florisil column chromatography (13×140 mm, hexane:ethyl acetate=3:2) to obtain 26.5 mg of the title compound.

$^1$H-NMR(CDCl$_3$): δ3.66 (1H, m), 4.4–4.7 (4H, Complex), 5.11 (1H, m), 6.71 (1H, d, J=1 Hz), 7.45 (4H, Complex), 7.58 (2H, Complex), 7.95–8.1 (4H, Complex), 8.14 (1H, s).

EXAMPLE 2

Preparation of (2α, 3α, 4β)-2-acetoxy-3,4-dibenzoyloxymethyloxetane (Compound 2)

11.7 mg of m-chloroperbenzoic acid was added to a solution of 11.2 mg of (2α, 3α, 4β)-2-acetyl-3,4-dibenzoyloxymethyloxetane (2α-isomer of Compound 6) in 1.5 ml of methylene chloride. The obtained mixture was stirred at 4° C. overnight to carry out the reaction. The reaction mixture was concentrated in a vacuum. The residue was purified with a preparative silica gel thin-layer plate (hexane:ethyl acetate=5:3) to give 10.2 mg of the title compound.

$^1$H-NMR(CDCl$_3$): δ2.12 (3H, s), 3.61 (1H, m), 4.53 (1H, dd, J=4.4, 12.7 Hz), 4.6–4.7 (3H, Complex), 5.07 (1H, m), 6.62 (1H, d, J=5.9 Hz), 7.44 (4H, Complex), 7.57 (2H, Complex), 7.9–8.1 (4H, Complex).

EXAMPLE 3

Preparation of (2β, 3α, 4β)-2-acetoxy-3,4-dibenzoyloxymethyloxetane (Compound 3)

7.0 mg of m-chloroperbenzoic acid was added to a solution of 6.6 mg of (2β, 3α, 4β)-2-acetyl-3,4-dibenzoyloxymethyloxetane (2β-isomer of Compound 6) in 0.8 ml of methylene chloride. The obtained mixture was stirred at 4° C. overnight to carry out the reaction. The reaction mixture was concentrated in a vacuum. The residue was purified with a preparative silica gel thin-layer plate (hexane:ethyl acetate=3:2) to obtain 5.0 mg of the title compound.

$^1$H-NMR(CDCl$_3$): δ2.06 (3H, s), 3.33 (1H, m), 4.48 (1H, dd, J=4.4, 13 Hz), 4.60 (2H, d, J=5.4 Hz), 4.67 (1H, dd, J=3.4, 13 Hz), 4.84 (1H, m), 6.38 (1H, d, J=3.9 Hz), 7.45 (4H, Complex), 7.58 (2H, Complex), 8.06 (2H, Complex), 8.14 (2H, Complex).

EXAMPLE 4

Preparation of (2α, 3α, 4β)-2-acetoxy-3-carbomethoxycarbonyloxymethyl-4-propionyloxymethyloxetane (Compound 4)

10.5 mg of m-chloroperbenzoic acid was added to a solution of 5.76 mg of (2α, 3α, 4β)-2-acetyl-3-carbomethoxycarbonyloxymethyl-4-propionyloxymethyloxetane (Compound 7) in 0.7 ml of methylene chloride. The obtained mixture was stirred at 4° C. overnight to carry out the reaction. The reaction mixture was concentrated in a vacuum to obtain a residue. This residue was purified with a preparative silica gel thin-layer plate (hexane:ethyl acetate=3:1) to give 5.16 mg of the title compound.

$^1$H-NMR(CDCl$_3$): δ1.15 (3H, t, J=7.5 Hz), 2.12 (3H, s), 2.38 (2H, q, J=7.5 Hz), 3.43 (1H, m), 3.88 (3H, s), 4.26 (2H, Complex), 4.57 (2H, d, J=7.5 Hz), 4.82 (1H, m), 6.47 (1H, d, J=6 Hz).

EXAMPLE 5

Preparation of oxetanocin (Compound 10)

A mixture of 5.16 mg of Compound (4) and 26 mg of molecular sieves 4A was stirred in 0.6 ml of 1,2-dichloroethane at room temperature for 2 hours, followed by the addition of 0.1 ml of tin tetrachloride and 39.61 mg of ditrimethylsilyl derivative of N-benzoyladenine. The obtained mixture was stirred for additional 2 hours to carry out the reaction. A saturated aqueous solution of sodium hydrogencarbonate was added to the reaction mixture and the generated precipitate was filtered off. The filter cake was washed with chloroform. The washings were combined with the filtrate. The obtained mixture was dried over anhydrous sodium sulfate and distilled in a vacuum to remove the solvent. The residue was dissolved in 2 ml of methanol, followed by the addition of 5 mg of sodium methoxide. The obtained mixture was stirred at room temperature overnight to carry out the reaction. After the completion of the reaction, the reaction mixture was concentrated in a vacuum to obtain a residue. This residue was reacted with an excess of benzoyl chloride in pyridine at room temperature for 3 hours to carry out the benzoylation. The reaction mixture was purified with a preparative silica gel thin-layer plate (benzene:ethyl acetate) to give 2.80 mg of oxetanosine tetrabenzoate (Compound 9).

Compound 9

Mass Calcd for $C_{31}H_{24}O_6N_5$ ($M^+$-Bz), m/z 562, 1724 found m/z 562, 1707.

IR(film):1710, 1695, 1570, 1490 cm$^{-1}$.

$^1$H-NMR(CDCl$_3$): δ4.36 (1H, m), 4.64 (1H, dd, J=4.9, 12.2 Hz), 4.70 (1H, dd, J=5.4, 12.7 Hz), 5.07 (1H, m), 6.61 (1H, d, J=5.9 Hz), 7.35 (4H, Complex), 7.45 (6H, Complex), 7.58 (2H, Complex), 7.85 (4H, Complex), 8.03 (4H, Complex), 8.32 (1H, s), 8.57 (1H, s).

8.6 mg of Compound (9) was dissolved in 1.2 ml of a 0.09N solution of sodium methoxide in methanol. The solution was reacted at room temperature for 7 hours. The obtained reaction mixture was adsorbed on an active carbon column (5×115 mm) and eluted with water, 20% aqueous acetone and 40% aqueous acetone (each in an amount of 20 ml) successively to give 3.1 mg of oxetanosine. The 400 MHz $^1$H-NMR spectrum of this oxetanosine was completely identical with that of natural one.

What is claimed is:

1. An oxetane derivative represented by the general formula (I):

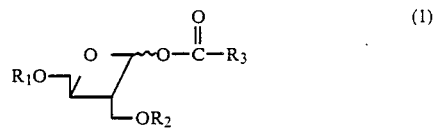

wherein $R_1$ and $R_2$ are each an acyl group and $R_3$ is a hydrogen atom or a lower alkyl group.

2. An oxetane derivative as set forth in claim 1, wherein said acyl group is a $C_{1\sim4}$ lower alkylcarbonyl group, a carbo-($C_{1\sim4}$)alkoxycarbonyl group of oxalate type, a ($C_{1\sim4}$)alkoxycarbonylmethylcarbonyl group of malonate type or an aromatic carbonyl group and $R_3$ is a hydrogen atom or a $C_{1\sim4}$ lower alkyl group.

3. An oxetane derivative as set forth in claim 1, wherein $R_1$ and $R_2$ are each a benzoyl, carbomethoxycarbonyl or propionyl group and $R_3$ is a hydrogen atom or a methyl group.

* * * * *